US012390149B2

(12) United States Patent
Subbalakshmi et al.

(10) Patent No.: US 12,390,149 B2
(45) Date of Patent: Aug. 19, 2025

(54) EXPLAINABLE CNN-ATTENTION NETWORK (C-ATTENTION NETWORK) ARCHITECTURE FOR AUTOMATED DETECTION OF ALZHEIMER'S DISEASE

(71) Applicant: THE TRUSTEES OF THE STEVENS INSTITUTE OF TECHNOLOGY, Hoboken, NJ (US)

(72) Inventors: Koduvayur P. Subbalakshmi, Holmdel, NJ (US); Mingxuan Chen, Jersey City, NJ (US); Ning Wang, Jersey City, NJ (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 405 days.

(21) Appl. No.: 18/022,981

(22) PCT Filed: Aug. 24, 2021

(86) PCT No.: PCT/US2021/047381
§ 371 (c)(1),
(2) Date: Feb. 23, 2023

(87) PCT Pub. No.: WO2022/046793
PCT Pub. Date: Mar. 3, 2022

(65) Prior Publication Data
US 2024/0023876 A1    Jan. 25, 2024

Related U.S. Application Data

(60) Provisional application No. 63/069,628, filed on Aug. 24, 2020.

(51) Int. Cl.
*A61B 5/00* (2006.01)

(52) U.S. Cl.
CPC .......... *A61B 5/4088* (2013.01); *A61B 5/4803* (2013.01); *A61B 5/7264* (2013.01)

(58) Field of Classification Search
CPC ... A61B 5/4088; A61B 5/4803; A61B 5/7264; G06N 3/045; G06N 3/08; G06F 40/216; G06F 40/268; G06F 40/284; G06F 40/289; G06F 40/30; G10L 25/30; G10L 25/66; G16H 50/70; G16H 50/20
See application file for complete search history.

(56) References Cited

PUBLICATIONS

International Search Report issued in for Int. Appln. No. PCT/US2021/047381 entitled "Explainable CNN-Attention Network (C-Attention Network) Architecture for Automated Detection of Alzheimer's Disease" (3 pages).
Written Opinion issued in Int. Appln. No. PCT/US2021/047381 entitled "Explainable CNN-Attention Network (C-Attention Network) Architecture for Automated Detection of Alzheimer's Disease" (8 pages).

(Continued)

*Primary Examiner* — Scott M. Getzow
(74) *Attorney, Agent, or Firm* — Clark Hill PLC; Ralph W. Selitto; John K. Kim

(57) ABSTRACT

Three artificial intelligence (AI) linguistic processing architectures are proposed for early detection of Alzheimer's Disease based entirely on a patient's language abilities. Three C-Attention network architectures are presented: one that uses only PoS features, one that uses only the latent features (e.g., language embeddings) and a unified architecture, which uses both features.

27 Claims, 3 Drawing Sheets

(56) References Cited

PUBLICATIONS

Ning Wang et al., "Explainable CNN-attention Networks (C-Attention Network) for Automated Detection of Alzheimer's Disease," medRxiv, Jun. 26, 2020, pp. 1-15, XP055865620 (16 pages).
PCT International Preliminary Report on Patentability for PCT/US2021/047381 entitled "Explainable CNN-Attention Network (C-Attention Network) Architecture for Automated Detection of Alzheimer's Disease" mailed on Feb. 28, 2023, 9 pages.

EXPLAINABLE CNN-ATTENTION NETWORK (C-ATTENTION NETWORK) ARCHITECTURE FOR AUTOMATED DETECTION OF ALZHEIMER'S DISEASE

CROSS-REFERENCE TO RELATED APPLICATION

This application is a U.S. National Phase entry under 35 U.S.C. 371 and claims priority to International Patent Application No. PCT/US2021/047381, filed on Aug. 24, 2021, which claims priority to U.S. Provisional Patent Application Ser. No. 63/069,628 filed Aug. 24, 2020, the entire disclosure of each of said applications being incorporated herein by reference.

STATEMENT REGARDING FEDERALLY SPONSORED RESEARCH

None.

FIELD OF THE INVENTION

The present invention relates to the detection of Alzheimer's Disease in patients, by evaluating their language abilities, in particular.

BACKGROUND OF THE INVENTION

In 2017, Americans spent $259B in caring for patients with Alzheimer's Disease (AD) and Related Dementia (ADRD). By the year 2050, these expenses are projected to reach $1 Trillion. The National Academy of Sciences, the National Plan to Address Alzheimer's Disease, and the Affordable Care Act through the Medicare Annual Wellness all identify earlier detection of ADRD as a core aim for improving brain health for millions of Americans. The success of disease modification and preventive therapeutics for ADRD requires the identification of the disease in very early stages, at least a decade before onset.

The traditional biological marker methods (e.g., neuroimaging, examination of cerebrospinal fluids, etc.) tend to be invasive, expensive and create patient compliance problems. Hence, there is a strong motivation to consider early detection schemes using noninvasive markers of the disease. On the other hand, using current cognitive assessment tools in primary care settings results in unrecognized cognitive disorders in 27%-81% of the affected patients Approaches to early identification have included the use of brief cognitive screening tests and biological markers (usually neuroimaging or cerebrospinal fluid examination). Neuroimaging modalities often include magnetic resonance imaging or the evaluation of positron emission tomography (PET) targeting amyloid, Tau or both proteins. Tracking every American for decades using these invasive and/or expensive techniques is infeasible and non-scalable. Also, the time course from a positive amyloid PET scan to ADRD in an older, cognitively normal adult often exceeds the duration of a clinical trial. Moreover, up to 30% of primary care patients refuse to undergo brief cognitive screening tests, and more than 70% of those who screened positive refuse to undergo a subsequent diagnostic follow-up.

Work on explainable artificial intelligence (AI) in general has started to emerge in importance specifically to address the problem of trustability of AI systems. However, none of the approaches used to date have provided precise, explainable results and/or ability to function specifically in natural language processing (NLP) domains.

Some previous efforts have used linguistic features, such as parts of speech (PoS) tags and syntactic complexity; psycholinguistic features (e.g., lexical and morphological complexity), word information, and readability, etc. to detect Alzheimer's Disease. One such approach used regression models to achieve an accuracy of 81% for discriminating between AD patients and healthy controls.

Known language processing methods include "Word2vec," "GloVe," and "sentence2vector." Word2vec is a technique for natural language processing. It uses aneural network model to learn word associations from a large corpus of text, which was presented in the paper entitled "Efficient Estimation of Word Representations in Vector Space," by Mikolov, Tomas et al., published in arXiv preprint arXiv:1301.3781(2013). GloVe is an unsupervised learning algorithm for obtaining vector representations for words. It was presented in the paper entitled "GloVe: Global Vectors for Word Representation," by Jeffrey Pennington et al., published in Proceedings of the 2014 conference on empirical methods in natural language processing (EMNLP) (2014). "sentence2vector" is a vector to represent a sentence instead of a word. It was presented in the paper entitled "Distributed Representations of Sentences and Documents" by Quoc Le et al., published in Proceedings of the 31st International Conference on Machine Learning (2014). The three publications above are incorporated herein by reference and made a part of the present application.

Some researchers have combined latent features obtained via language embeddings like 'word2vec,' 'GloVe,' 'sentence2vector,' along with hand-crafted features in a hybrid approach using a Convolutional Neural Network (CNN) and Recurrent Neural Network (RNN) architecture to achieve varying accuracies around 89%.

While the above methods show varying degrees of accuracy, they do not provide adequate explainability in their models. Some researchers have introduced visualizations to help move the research in the direction of explainability. Activation clusters and first derivative saliency heat maps were previously used, and K-means clustering has been used to find the most frequently used topic in text data. Explainable AD models have been developed for MRI based AD detection methods, which have previously proposed a gradient-based visualization method to detect the most important biomarkers related to AD and progressive mild cognitive impairment (pMCI). However, these are not applicable to language-based detection.

SUMMARY

Artificial intelligence models have been developed for diagnosis of Alzheimer's Disease and form a basis of the present invention. Specifically, the present invention encompasses three explainable architectures using CNN and attention to detect Alzheimer's Disease using two kinds of features: PoS and language embeddings. One architecture uses only the PoS feature, one uses only the universal sentence embedding (USE), and the third is a unified architecture that uses both of these features. In one embodiment, attention layers are used at three levels: one each at the intra-feature level for each type of feature and one at the inter-feature-class level. The intra-feature level attention weights capture the relative importance the model places on the individual features in the category, whereas the inter-feature level attention weights give an idea of the relative importance that the model places between the two classes of features.

In an embodiment, the present invention proposes three explainable deep learning architectures to automatically detect patients with Alzheimer's Disease based on their speech patterns. These architectures use: (1) only parts-of-speech features obtained from the patient's description; (2) only language embedding features; and (3) both of these feature classes via a unified architecture. Self-attention mechanisms and one-dimensional CNN are used to generate two types of explanations of the model's action: intra-class explanation and inter-class explanation. The intra-class explanation captures the relative importance of each of the different features in that class, while the inter-class explanation captures the relative importance between the classes. Furthermore, the architecture is easily expandable to additional classes of features because of its modularity. So, if newer features (FT) are discovered as being important to the detection of AD, they can be added onto the architecture proposed herein.

Extensive testing on the popular DementiaBank datasets and comparisons with several recently published models as well as minor modifications of the models of the present invention show that the C-Attention-FT architecture performs best in terms of accuracy and F1 scores and that the C-attention-FT+Embedding performs best in terms of precision and AU, while at the same time being able to generate explanations of the action of the AI. F1 scores are defined as the harmonic mean of precision and recall, wherein precision is defined as the closeness of the measurements to each other (i.e., defined as the number of true positives divided by the number of true positives plus the number of false positives) and recall is defined as the number of true positives divided by the number of true positives plus the number of false negatives.

Overall, the present invention is an inexpensive, non-invasive, explainable AI model that can detect AD at good performance metric. Since it is based on only the spoken language, it can be potentially easily implemented in an app setting by giving the option of taking it at home. This in turn can have a positive impact on patient compliance.

This invention can be implemented in anon-threatening atmosphere such as a patient's own home and is non-invasive, because it is only dependent on the patient's language abilities. These factors will contribute to better adherence of the patient to testing, early detection and potential early intervention while being orders of magnitude cheaper to implement.

In an embodiment, the present invention can be implemented as an app that can run on a mobile phone or a device such as Alexa, Google Home or the like.

The present invention also has applicability to the detection of other mental disorders, which may be detected with appropriately modified "handcrafted features." Furthermore, the current architecture can be extended to more handcrafted features that may be discovered in the future as being relevant to Alzheimer's Disease.

BRIEF DESCRIPTION OF FIGURES

For a more complete understanding of the present disclosure, reference is made to the following figures, in which.

DETAILED DESCRIPTION OF EXEMPLARY EMBODIMENTS

Reference will now be made to several embodiments of the present invention, examples of which are illustrated in the accompanying figures. Wherever practicable, similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

All terms defined herein should be afforded their broadest possible interpretation, including any implied meanings as dictated by a reading of the specification as well as any words that a person having skill in the art and/or a dictionary, treatise, or similar authority would assign thereto.

The terms, "for example", "e.g.", "optionally", as used herein, are intended to be used to introduce non-limiting examples. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on." In addition, the terms "comprises" and "comprising" when used herein specify that certain features are present in that embodiment; however, this phrase should not be interpreted to preclude the presence or addition of additional steps, operations, features, components, and/or groups thereof.

The present invention introduces C-Attention architectures useful for early, non-invasive diagnostics of Alzheimer's Disease. Three architectures are presented: one that uses only PoS features, one that uses only the latent features (e.g., language embeddings) and a unified architecture, which uses both features.

Figure 1:
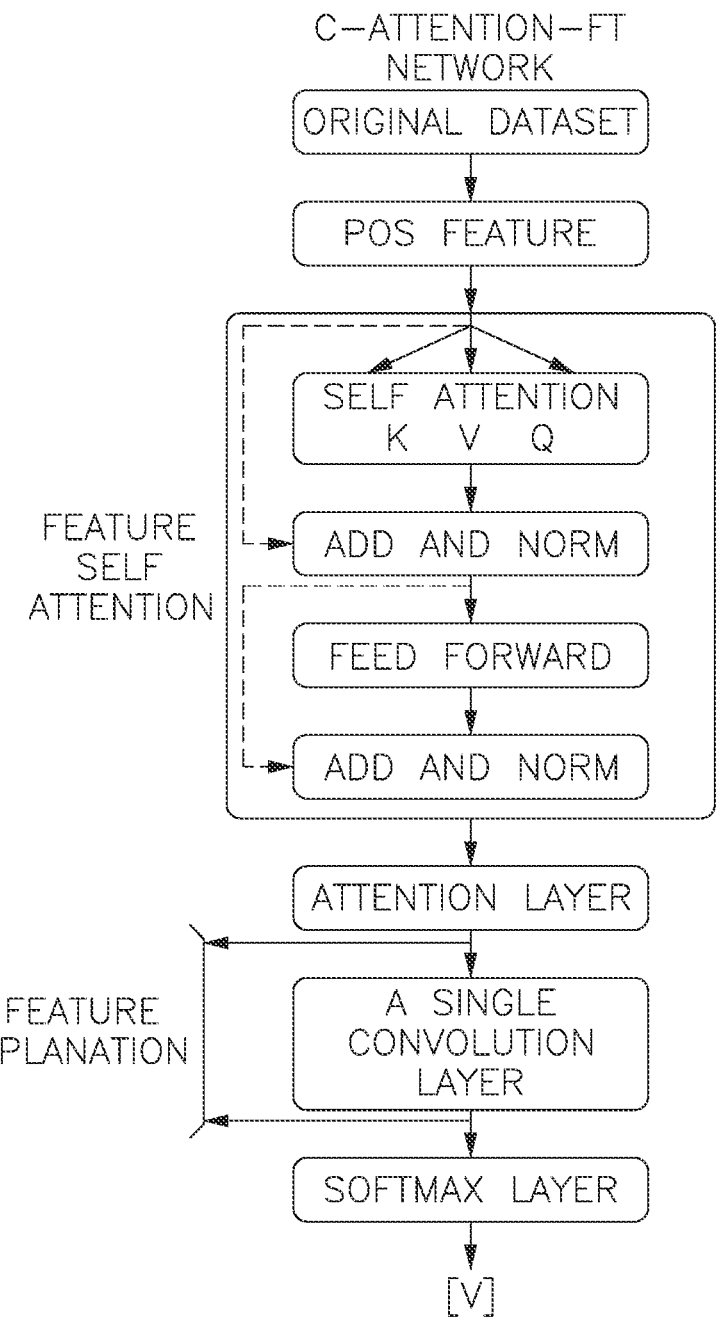
FIG. 1 is a model architecture used for exploiting PoS features in accordance with an embodiment of the present invention.

FIG. 1 schematically represents the proposed architecture of a C-Attention-FT Network that uses PoS features. This architecture involves a self-attention module that captures the intra-feature relationships; an attention layer followed by a single convolution layer that can be used to generate feature level explanations and a softmax layer. Softmax is a function that takes as input a vector z of K real numbers and normalizes it into a probability distribution consisting of K probabilities proportional to the exponentials of the input numbers. The Multi-Head-Attention (MHA) module described hereinbelow is based on the popular transformer architecture presented in the paper entitled "Attention is All you Need," by Ashish Vaswani et al., published in Advances in Neural Information Processing Systems 30, 2017, the entire contents of which publication being incorporated by reference and made a part of the present application. More details on the MHA module are given hereinbelow. Given R={$r_1$, $r_2$, $r_n$} is the set of records, then $r_1$ is the ith record in the dataset. PoS tags are computed for each record using NLTK, as discussed in the publication by Fraser et al. entitled "Linguistic Features Identify Alzheimer's Disease in Narrative Speech," published in the Journal of Alzheimer's Disease 49 (2), the entire contents of which publication are incorporated herein by reference and made a part of the present application. Given P={$p_1$, $p_2$, $p_n$} is the set of PoS feature vectors and $p_1$ is the ith vector in the PoS matrix, a total of h MHA layers are used on P={$p_1$, $p_2$, $p_n$} to capture the relationship between the PoS features. The MHA transforms P={$p_1$, $p_2$, $p_n$} to another matrix of n-dimensional vectors A={$a_1$, $a_2$, $a_n$}. The MHA module is followed by a 1-layer CNN and a softmax layer to get the final classification.

Figure 2:
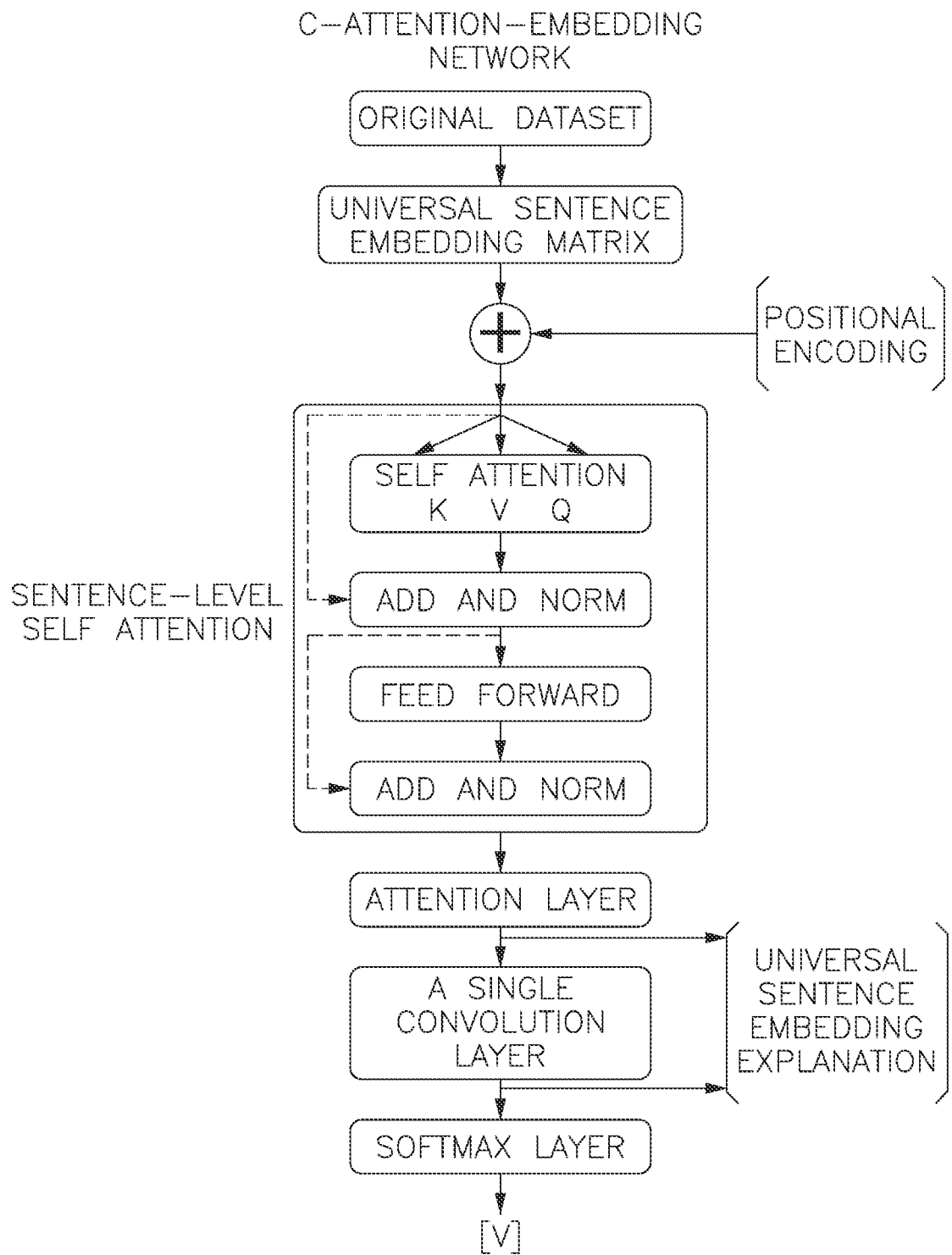
FIG. 2 is a model architecture used for exploiting latent features in accordance with an embodiment of the present invention.

Turning now to FIG. 2, it schematically represents the proposed architecture of a C-Attention-Embedding Network that uses the sentence embeddings of the patient/control's description. This architecture is proposed as a means of capturing latent feature information implicit in language embeddings. Specifically, USE is used to represent each sentence in a record. USE is discussed in the publication by Cer et al. entitled "Universal Sentence Encoder" in arXiv preprint arXiv:1803.11175 (2018), the entire contents of which publication are incorporated herein by reference. This architecture is similar to the proposed C-Attention network of FIG. 1, except for the addition of a positional encoding module. The positional encoding module is used to maintain the relative positions of the sentences and is the same as that used in the transformer architecture described in the aforementioned Vaswani publication. The designation ui is the USE vector corresponding to the ith sentence in the record. The positional encoding is applied to each vector and the resulting vectors, u' i, are used to construct the matrix U={$u_1'$, $u_2'$, . . . , $u_n'$}. An h-layer MHA module is used to extract the intra-feature relationships in this architecture. This is followed by $a_n$ attention layer that captures interpretation at the embedding feature level. The output of the attention layer is fed to a 1-layer CNN and a softmax to get the final prediction.

Figure 3:
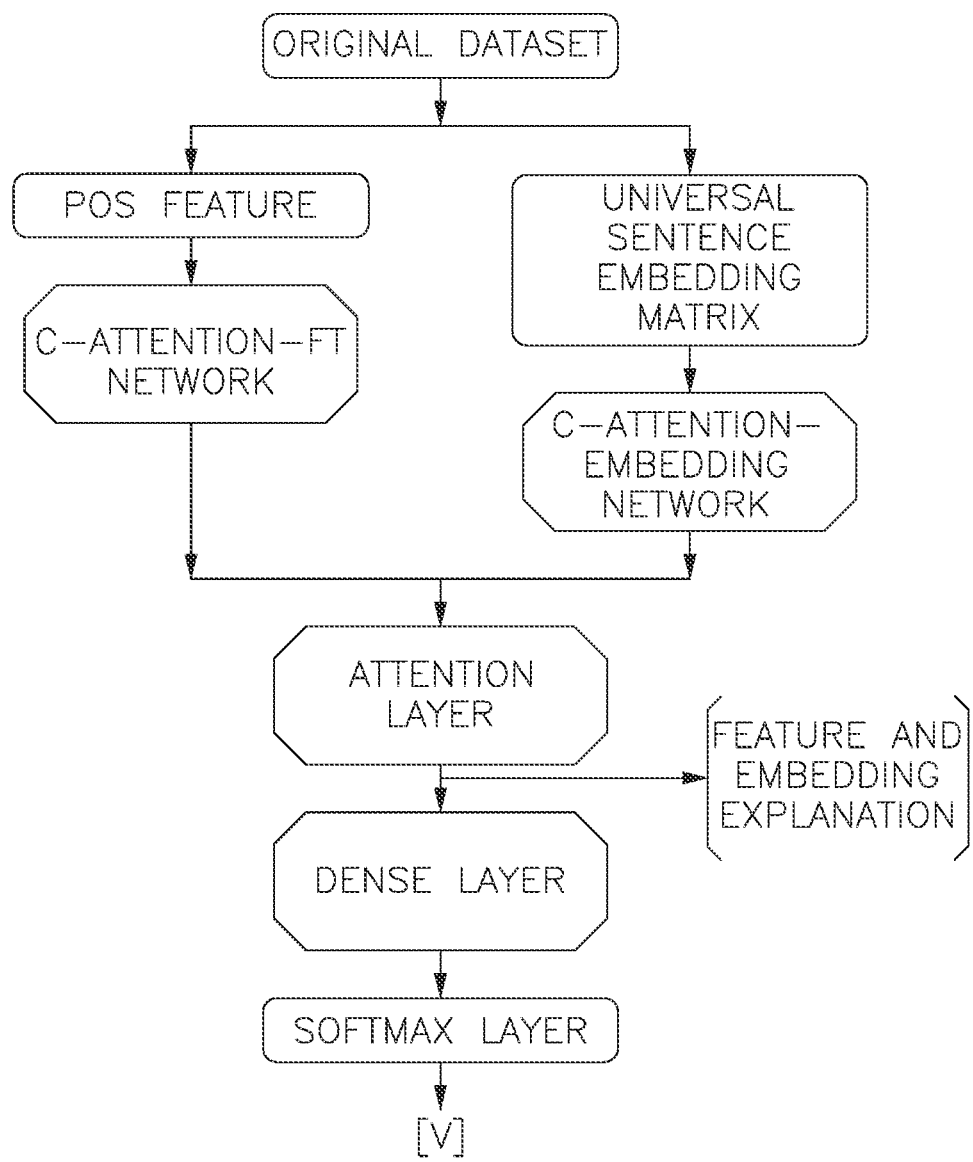
FIG. 3 is a model architecture used for processing both PoS and latent features in accordance with an embodiment of the present invention.

FIG. 3 schematically depicts a Unified C-Attention Network architecture that uses the proposed C-Attention-FT network of FIG. 1 and the C-Attention-Embedding network of FIG. 2 as two "legs" and combines them with another attention layer followed by a dense layer and the softmax layer. The dense linear layer is the same as that proposed in the transformer architecture of the Vaswani publication. The attention layer captures the relative importance between the PoS and the USE features and helps in providing an interpretation at the feature class level.

Attention mechanisms have proven to be efficient in capturing global dependencies without any restrictions on the distance between the input and output sequences (see for instance the publications entitled "Neural Machine Translation by Jointly Learning to Align and Translate," published in arXiv preprint arXiv:1409.0473 (2014), and "Vector-Space Topic Models for Detecting Alzheimer's Disease," published In Proceedings of the $54^{th}$ Annual meeting of the Association for Computational Linguistics (Vol 1: Long Papers), both of which publications are incorporated by reference and made a part of the present application. Self-attention mechanisms, along with positional coding in the design of the transformer have become very popular in language models like BERT. One such self-attention mechanism is described in the publication entitled "A Decomposable Attention Model for Natural Language Inference," published in arXiv preprint arXiv:1606.01933 (2016), the entire contents of which publication are incorporated herein by reference and made a part of the present application. In an embodiment of the present invention, the attention mechanisms and MHA mechanism proposed in the Vaswani publication may be used. These mechanisms use a scaled dot product attention, which is given by Attention $$(Q, K, V) = \text{softmax}\left(\frac{QK^T}{\sqrt{dk}}\right)V$$

where Q,K and V are the query, key and value matrices, respectively, and dk is dimension of the query and key vectors.

CNNs' classify text function is commonly done as follows: in a single convolutional layer, filters are used to detect ngrams (i.e., contiguous sequences of n items from a given sample of text or speech), and each filter detects a closely-related family of ngrams. Then the following max-pooling layer extracts the relevant ngrams to make the final decision. In one embodiment of the present invention, a 1 gram filter in the PoS leg is used to detect each PoS feature, and 1 gram and 2 grams filters are used in the embedding leg to detect within each sentence, as well as each two continuous sentences.

The present invention is further described in the example that follows, and supplementary details are contained in the publication Explainable CNN-attention Networks (C-Attention Network) for Automated Detection of Alzheimer's Disease, the entire contents of which are incorporated by reference herein.

Example 1

The proposed C-Attention Network architectures were evaluated with respect to the DementiaBank dataset, and the performances of architectures of the present invention were compared with each other, as well as with some recently published results. Extensive testing on the popular DementiaBank datasets and comparisons with several recently published models as well as minor modifications of the models of the present invention showed that the proposed C-Attention-FT architecture performs the best in terms of accuracy and F1 scores, and the proposed C-attention-FT+ Embedding performs best in terms of precision and AUC, while at the same time being able to generate explanations of the action of the AI.

The proposed model in accordance with an embodiment of the present invention was implemented by using the open source machine learning library' Pytorch.' The model was trained to minimize the cross-entropy loss function of predicting the class label of participants' speech records in the training set.

As mentioned above, two types of features were extracted: part of speech (PoS) and sentence embedding. For all models in the experiments, there were 6 layers for the multi-head attention (MHA) module. Stochastic gradient descent and momentum (i.e., SGD+Momentum) as the optimizer for training. Since the DementiaBank dataset is unbalanced, a class weight correction was included increasing the penalty for misclassifying the less frequent class during model training to reduce the effect of data bias. The class weight correction ratio used was 7:3. The average number of utterances in this dataset is 17. In order to have a fixed number of utterances in our model, the number of utterances was set as 17. Extra utterances for descriptions that had more than 17 utterances were truncated and padding was added for those with less than 17 utterances. It is noted that changing this number to the median number of utterances or the maximum number of utterances did not give better results. The original data was randomly distributed into 81% training, 9% validation and 10% testing.

An advantage of models made in accordance with embodiments of the present invention is that the classification interpretation can be explained. Specifically, for each case, it can be explained whether the model considers the PoS features or the latent feature as more important in its decision. Similarly, the self-attention weights can be used to determine the relative importance of utterances within a patient's record and the relative importance of the different PoS features in arriving at the final decision.

Regarding USE features, it was found the sentences that are considered most important by the attention layer (i.e., those that have the highest attention values) are almost always captured by the filters in the 1-D CNN layer. 121 speeches out of 129 speech samples show this pattern. Additionally, it was noted that the intra-feature attention value for a patient's utterances seems to be more uniformly distributed compared to those of a healthy control, which shows a definite higher value for some sentences compared to others. This might indicate that the AI is picking up on the "randomness" of the utterances of the patients compared to that of a healthy control.

Regarding the PoS features, they were extracted at speech level. A total of 36 PoS tags were defined. Like the latent features, the PoS features with the highest attention weight were 100% captured by the filters in the following 1-D CNN layer. The entire testing dataset was then analyzed. This analysis would indicate that the PoS features NNPS (proper noun, plural), MD (modal), EX (existential) and PRP (personal pronoun) are the most important features, accounting for 80.9% of times for the PoS Features. These findings are consistent with previous works that found that AD patients tend to use more pronouns instead of nouns compared with healthy controls To explain the relative importance of feature classes (i.e., PoS vs latent features): The final attention layer of the proposed unified C-Attention-FT+Embedding architecture (See FIG. 3), captures the relative importance between the PoS features and the latent features in a decision. For certain speech records, the latent features played a bigger role than PoS features in determining the overall decision with a larger embedding weight. In contrast, for other records, the PoS feature was weighted more than the latent features. From the results, 65.1% of the cases were assigned a higher attention value, while Universal Sentence Embedding was assigned a higher attention value in 34.9% of the cases, indicating that the PoS features seem to play a larger role in detecting AD.

The present invention thus constitutes an inexpensive, non-invasive, explainable AI model that can detect AD at a good performance metric. Since the inventive model is based on only the spoken language, it can be potentially easily implemented and have a positive impact on patient compliance and early detection of AD.

It will be understood that the embodiments described herein are merely exemplary and that a person skilled in the art may make many variations and modifications without departing from the spirit and scope of the invention. All such variations and modifications are intended to be included within the scope of the present invention as it is explicitly and inherently described hereinabove and as illustrated in the accompanying drawings.

What is claimed is:

1. A method of speech analysis for medical diagnostics, comprising the steps of:
 a) obtaining a speech sample from a patient;
 b) classifying said speech sample with a plurality of parts of speech tags;
 c) applying a self-attention module to said plurality of parts of speech tags;
 d) applying an attention layer to said plurality of parts of speech tags;
 e) applying a convolution layer to said plurality of parts of speech tags;
 f) applying a softmax layer to said plurality of parts of speech tags;
 g) generating an intra-class explanation of said speech sample from data derived from the performance of steps c) through f); and
 h) determining a diagnosis of a medical condition.

2. The method of claim 1, wherein said self-attention module comprises a multi-head attention layer.

3. The method of claim 2, wherein said multi-head attention layer comprises six layers.

4. The method of claim 2, wherein said multi-head attention layer is configured to apply scaled dot product attention.

5. The method of claim 1, wherein said medical condition is Alzheimer's disease.

6. The method of claim 1, further comprising the step of applying a class weight correction to said speech sample.

7. The method of claim 1, wherein said steps d) and e) are performed simultaneously.

8. The method of claim 1, wherein said diagnosis is based on said intra-class explanation.

9. A method of speech analysis for medical diagnostics, comprising the steps of:
 a) obtaining a speech sample from a patient;
 b) representing said speech sample as universal sentence embeddings;
 c) applying a self-attention module to said universal sentence embeddings;
 d) applying an attention layer to said universal sentence embeddings;
 e) applying a convolution layer to said universal sentence embeddings;
 f) applying a softmax layer to said universal sentence embeddings;
 g) generating an intra-class explanation of said speech sample from data derived from the performance of steps c) through f); and
 h) determining a diagnosis of a medical condition.

10. The method of claim 9, wherein said self-attention module comprises a multi-head attention layer.

11. The method of claim 10, wherein said multi-head attention layer comprises six layers.

12. The method of claim 10, wherein said multi-head attention layer is configured to apply scaled dot product attention.

13. The method of claim 9, further comprising the step of applying a positional encoding module to said universal sentence embeddings.

14. The method of claim 9, wherein said medical condition is Alzheimer's disease.

15. The method of claim 9, further comprising the step of applying a class weight correction to said speech sample.

16. The method of claim 9, wherein said steps d) and e) are performed simultaneously.

17. The method of claim 9, wherein said diagnosis is based on said intra-class explanation.

18. A method of speech analysis for medical diagnostics, comprising the steps of:
   a) obtaining a speech sample from a patient;
   b) classifying said speech sample with a plurality of parts of speech tags;
   c) representing said speech sample as universal sentence embeddings;
   d) applying a first self-attention module to said universal sentence embeddings to obtain first data;
   e) applying a second self-attention module to said plurality of parts of speech tags to obtain second data;
   f) applying a first attention layer to said first data;
   g) applying a first convolution layer to said first data;
   h) applying a first softmax layer to said first data;
   i) applying a second attention layer to said second data;
   j) applying a second convolution layer to said second data;
   k) applying a second softmax layer to said second data;
   l) applying a third attention layer to said first data and said second data to obtain third data;
   m) applying a dense layer to said third data;
   n) applying a third softmax layer to said third data;
   o) generating an intra-class explanation from said third data from data derived from the performance of steps l) through n);
   p) generating an inter-class explanation from said third data from data derived from the performance of steps l) through n); and
   q) determining a diagnosis for a medical condition.

19. The method of claim 18, further comprising the step of determining relative importance between said plurality of parts of speech tags and said universal sentence embeddings.

20. The method of claim 18, wherein said first attention module comprises a multi-head attention layer.

21. The method of claim 20, wherein said multi-head attention layer comprises six layers.

22. The method of claim 20, wherein said multi-head attention layer is configured to apply scaled dot product attention.

23. The method of claim 18, further comprising the step of applying a positional encoding module to said universal sentence embeddings.

24. The method of claim 18, wherein said medical condition is Alzheimer's disease.

25. The method of claim 18, wherein said steps f) and g) are performed simultaneously.

26. The method of claim 18, wherein said steps i) and j) are performed simultaneously.

27. The method of claim 18, wherein said diagnosis is based on said intra-class explanation and said inter-class explanation.

* * * * *